US00PP11078P

United States Patent [19]

Mathews

[11] Patent Number: Plant 11,078

[45] Date of Patent: Oct. 5, 1999

[54] CHILOPSIS PLANT NAMED 'MONHEWS'

[75] Inventor: Richard Mathews, Bisbee, Ariz.

[73] Assignee: Monrovia, Azusa, Calif.

[21] Appl. No.: 09/006,710

[22] Filed: Jan. 14, 1998

[51] Int. Cl.[6] ..... A01H 5/00

[52] U.S. Cl. ..... Plt./216

[58] Field of Search ..... Plt./216, 226

*Primary Examiner*—Howard J. Locker
*Assistant Examiner*—Kent L. Bell

[57] ABSTRACT

A new and distinct selection of Desert Willow, *Chilopsis linearis,* which shall be referred to hereinafter as cultivar 'Monhews'. Cultivar 'Monhews' differs distinctively from other *Chilopsis linearis* plants known to the inventor by possessing a unique combination of showy two-toned flowers, long bloom season and fewer and smaller seed pods containing sterile seed. This unique characteristic of sterile seed and fewer and smaller seed pods results in a landscape plant, which is much cleaner and may be reason for the desirable longer bloom period.

2 Drawing Sheets

BACKGROUND OF THE INVENTION

This invention relates to a new and distinct selection of *Chilopsis linearis,* a member of the Bignoniaceae family. Cultivar 'Monhews' was discovered as a seedling of unknown parentage in 1994 from seed I had sown in the winter of 1992. My discovery was initially noticed in its first year of growth as it produced a heavy abundance of flowers for an unusually long period of time when compared to other Chilopsis plants known to me. The second year during bloom time I realized how notable this new plant was. The third year bloom season I noted the sterile seed and unusually small and few pods. My new plant has been asexually reproduced by cuttings since the discovery at my residence in Bisbee, Ariz. and later at Monrovia, 18331 E. Foothill Boulevard, Azusa, Calif.

My discovery substantially differs from other *Chilopsis linearis* plants known to me by the unique characteristic of sterile seed which results in fewer and smaller seed pods, therefore a cleaner tree with a prolonged and more intense bloom season. These characteristics set the claimed plant apart from other cultivars of *Chilopsis linearis* which I am aware. Had the initial seedling not been discovered by me it may have been lost to mankind. It is unlikely the favorable attributes of this plant could be conveyed to progeny through sexual reproduction. However, through extensive asexual propagation by rooting cuttings of this plant it has been established that the novel, exceptional characteristics are stable and reliably passed on from generation to generation by such means.

SUMMARY OF INVENTION

*Chilopsis linearis* cultivar 'Monhews' is the only sterile Desert Willow to my knowledge. The Desert Willow is widely used in landscapes in the south western United States, its native range. Plants bloom early and are tolerant of heat, cold, drought and wind. The main landscape disadvantage are messy 15–30 cm long seed pods which litter surrounding areas and hang on the tree during its winter dormancy.

My discovery has overcome this most objectionable concern of *Chilopsis linearis* which makes this adaptable and more landscape desirable. Seed pods on 'Monhews' plants do exist however, they are few in number and range from 2.5 cm to 4 cm in length with $1/20^{th}$ the mass of a typical *Chilopsis linearis* seed pod.

The flowering season is unusually long from May continuously through September in Bisbee, Ariz. Typically *Chilopsis linearis* bloom from May until June, then sporadically and briefly with rainfall. It is believed the sterility factor allows this plant to produce almost three times more flowers for a longer period of time as energy is not required for seed production.

BOTANICAL DESCRIPTION

Figure 1:
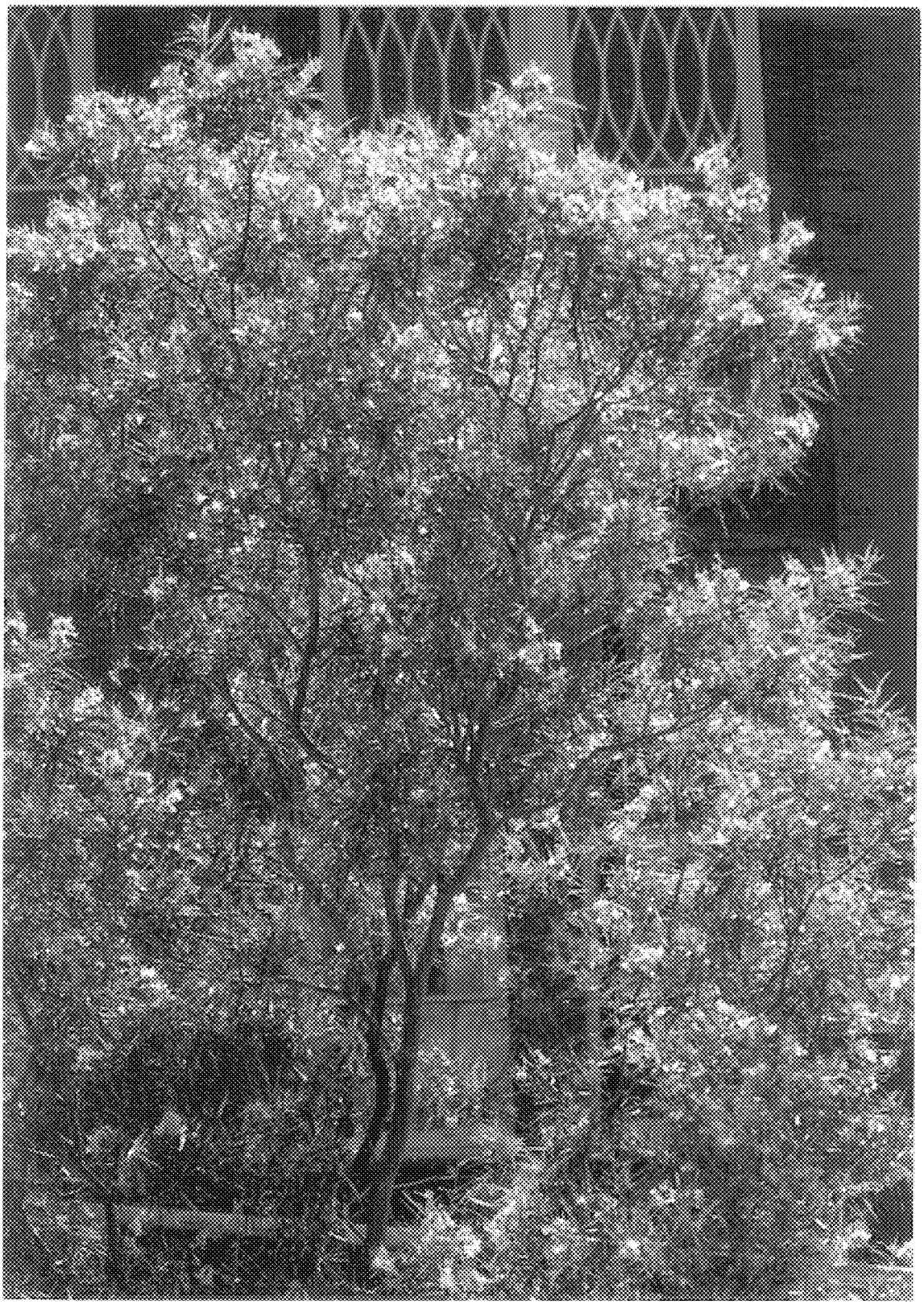
FIG. 1 — Depicts the overall tree — like habit with bloom.
Figure 2:
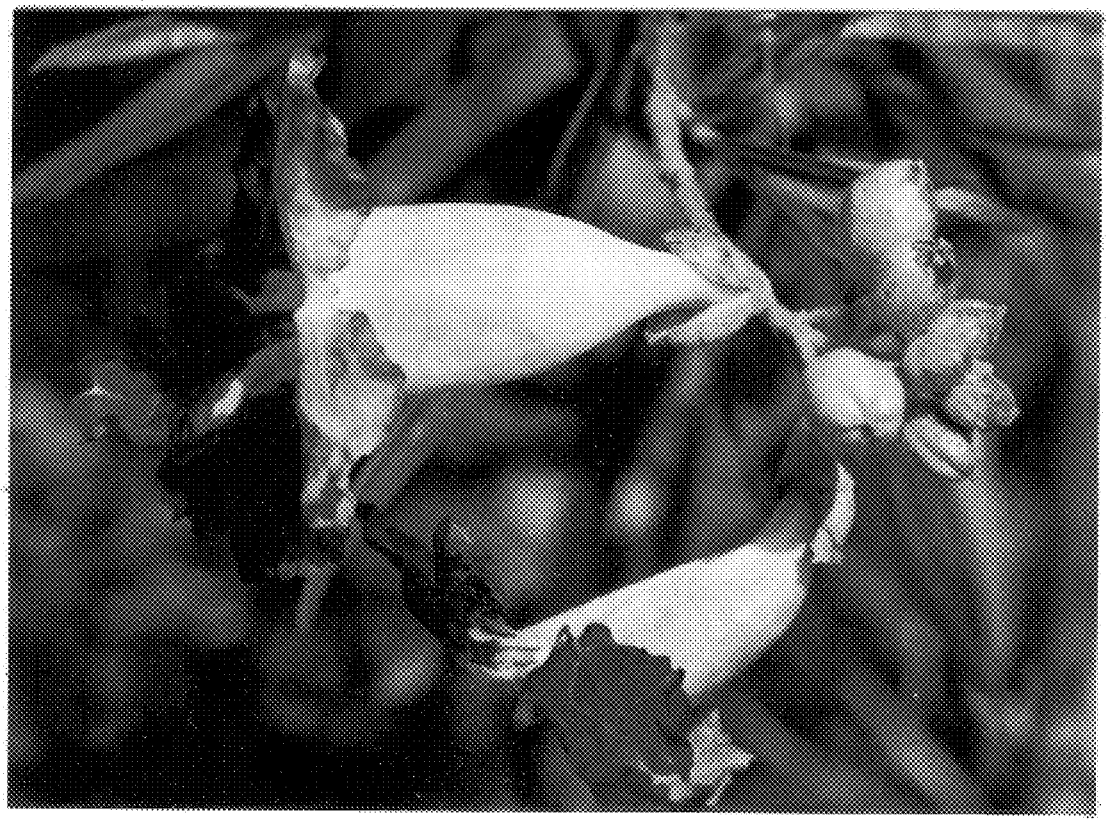
FIG. 2 — Depicts a close up view of the two-toned corolla lobes.
Figure 3:
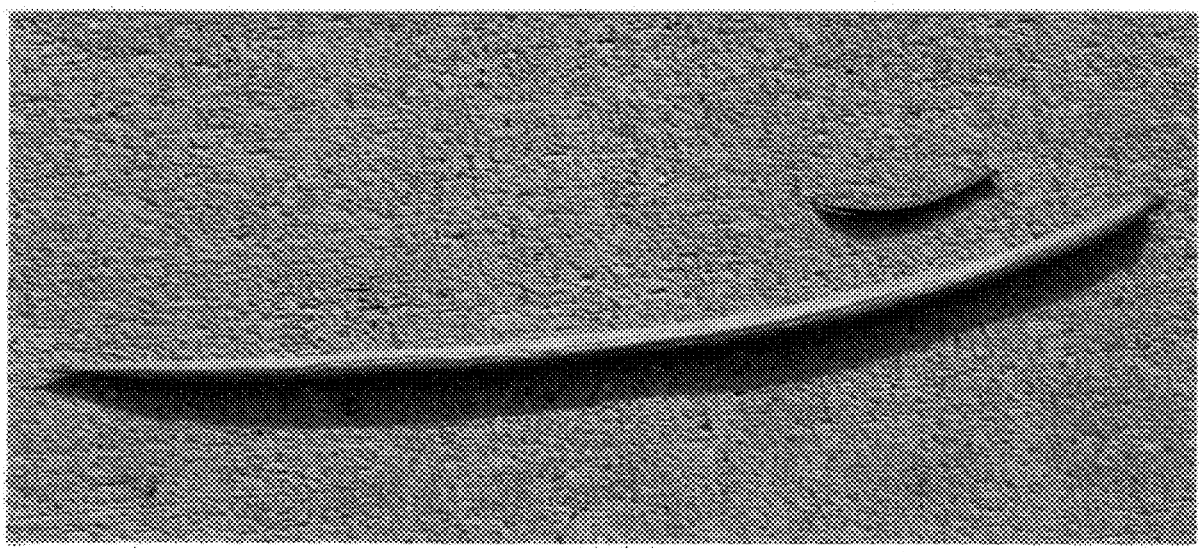
FIG. 3 — Depicts the size comparison of a small seed pod of my selection above and an average size seed pod of a typical Chilopsis plant.

Below is a detailed description of my selection of *Chilopsis linearis* cv. 'Monhews', the color terminology is from The Royal Horticultural Society Colour Chart. Plant size and description are based on plants growing in Bisbee, Ariz. elevation 3,500 feet.

Overall size: Five years of age on unimproved soil without irrigation tree is 4 meters tall and 3.5 meters wide. Ultimate size is estimated to be 8 to 10 meters tall and 8 meters wide.

Overall habit: Deciduous, graceful tree. More tree-like and less shrubby than many Desert Willows. Blooms for a longer duration with three times more flowers than the typical Desert Willow.

Foliage:

*Length.*—7.5 cm to 12.5 cm.

*Width.*—0.6–1.1 cm.

*Color.*—Mature: upper: Green Group 138A. lower: Green Group 138A. Juvenile: upper: Yellow Group 144A. lower: Yellow Group 144A.

*Surface.*—Nitidus, polished, glabrous.

*Arrangement.*—Opposite.

*Texture.*—Semi-coriaceous.

*Margins.*—Entire.

*Shape.*—Narrow-lanceolate or linear.

*Apex.*—Acuminate.

*Base.*—Cuneate.

Stem:

*Pubescense.*—None. Conspicous lenticels along stem.

*Color.*—Juvenile — Yellow Green Group 144B, recent growth no lenticels. Current year growth — Greyed Orange Group 166A. Mature — Greyed Green Group 197C and 197B, texture smooth except for lenticels.

*Lenticels.*—Number — Abundant. Size — 1–13 mm in length. Color — Greyed Green Group 197D.

*Fruit.*—Type: pod, 2-valved, cylindric. Length: 4 to 4.5 cm long×2 mm wide (normal typical Chilopsis pods range from 15–30 cm long and 5 mm to 6 mm thick).

*Flower.*—Production: extremely limited, 7-year-old tree produced twelve seed pods. Seeds are sterile. Arrangement: short terminal panicles. Shape at anthesis: bilabiate, trumpet shaped. Shape at aestivation (flower bud): corolla lobes fold inward. Flower bud: length 4½ cm, width 2 cm, color purple Group 76D. Color: lower 2 lobes darkest Purple Group 77A. upper lobes: Purple Group 76D with margins edged darker Purple 77B. Outer corolla: Purple Group 77 D,C,B. Tube and throat: 2 Yellow stripes, Yellow Group 3A run length of corolla tube and 3 mm wide. Five to Seven stripes of Purple Group 77A run length of corolla tube 1 mm wide, background color Purple Group 76D. Corolla size: length 5 cm. width 3½ cm. Corolla lobes: jagged, 5 and crimped. Calyx: 3–4 parted. Fragrance: None detected

*Reproductive.*—Stamens: 4 anther bearing, a fifth rudimentary. Style: 2.6 cm–3.0 cm in length.

I claim:

1. A new and distinct selection of *Chilopsis linearis* plant as substantially shown and described herein, that is characterized particularly as a novelty by the unique combination of showy two-toned flowers, long bloom season and fewer and smaller seed pods containing sterile seeds.

* * * * *